(12) United States Patent
Day et al.

(10) Patent No.: US 9,759,724 B2
(45) Date of Patent: *Sep. 12, 2017

(54) DEVICE FOR DETECTION OF MOLECULES IN BIOLOGICAL FLUIDS

(71) Applicant: Instant Medical Diagnostics, LLC, Potomac, MD (US)

(72) Inventors: Alan R. Day, North Potomac, MD (US); Allan M. Weinstein, Potomac, MD (US); Bryan C. Christiansen, Germantown, MD (US)

(73) Assignee: INSTANT MEDICAL DIAGNOSTICS, LLC, Potomac, MD (US)

( * ) Notice: Subject to any disclaimer, the term of this patent is extended or adjusted under 35 U.S.C. 154(b) by 827 days.

This patent is subject to a terminal disclaimer.

(21) Appl. No.: 14/138,885

(22) Filed: Dec. 23, 2013

(65) Prior Publication Data

US 2014/0113280 A1   Apr. 24, 2014

Related U.S. Application Data

(63) Continuation of application No. 12/830,498, filed on Jul. 6, 2010, now Pat. No. 8,614,102, which is a continuation of application No. 11/833,796, filed on Aug. 3, 2007, now Pat. No. 7,749,773.

(60) Provisional application No. 60/851,130, filed on Oct. 11, 2006.

(51) Int. Cl.
| | | |
|---|---|---|
| *G01N 33/569* | (2006.01) | |
| *G01N 33/543* | (2006.01) | |
| *G01N 21/64* | (2006.01) | |
| *G01N 21/84* | (2006.01) | |
| *G01N 33/558* | (2006.01) | |

(52) U.S. Cl.
CPC ... *G01N 33/56983* (2013.01); *G01N 21/6428* (2013.01); *G01N 21/8483* (2013.01); *G01N 33/54306* (2013.01); *G01N 33/558* (2013.01); *B01F 2215/0037* (2013.01); *Y10S 436/807* (2013.01); *Y10S 436/81* (2013.01)

(58) Field of Classification Search
CPC ...... B01F 2215/0037; G01N 33/56983; G01N 33/54306; G01N 21/6428; G01N 21/8483; G01N 33/558; G01N 2035/00108; G01N 2021/7759; G01N 2035/00128; G01N 2035/00118; G01N 33/54386; B01L 2300/00825; Y10S 435/97

See application file for complete search history.

(56) References Cited

U.S. PATENT DOCUMENTS 8,614,102 B2 * 12/2013 Day .................. G01N 21/6428 436/514

\* cited by examiner

*Primary Examiner* — Christine Foster
(74) *Attorney, Agent, or Firm* — Richard M. Klein; Fay Sharpe LLP

(57) ABSTRACT

Disclosed is a test device and a method for qualitatively and/or quantitatively measuring the concentration of an analyte in a biological fluid sample. The test device includes a housing defining a sample port, a test well containing a stirrer and a conjugate, and a test strip disposed within the housing. The test well is also defined by being located between the sample port and the test strip. Fluid flows from the test well onto the test strip, which has a trapping zone which binds the analyte and allows for its detection. A control zone may also be included. The test device is generally adapted to use a sandwich assay. Also disclosed is a system comprising the test device and a signal sensing device; and a method for using the test device.

13 Claims, 4 Drawing Sheets

DEVICE FOR DETECTION OF MOLECULES IN BIOLOGICAL FLUIDS

CROSS-REFERENCE TO RELATED APPLICATIONS

This application is a continuation of U.S. patent application Ser. No. 12/830,498, filed Jul. 6, 2010, now U.S. Pat. No. 8,614,102, which is a continuation application of U.S. patent application Ser. No. 11/833,796, filed Aug. 3, 2007, now U.S. Pat. No. 7,749,773, which claimed priority to U.S. Provisional Patent Application Serial No. 60/851,130, filed Oct. 11, 2006. The entire contents of that provisional application are hereby incorporated by reference.

BACKGROUND

The present disclosure relates to assays for detecting or quantifying the concentration of large and small molecules in biological fluids. The disclosure also relates to devices used in such assays and methods for making and using them.

Many types of large and small molecules can be detected in biological fluids. Such molecules may include enzymes, viruses, proteins, hormones, antibodies, antigens, and various biological waste products. For example, some specific molecules include human chorionic gonadotropin, ICAM, VCAM, integrin, fibrin, and prostate-specific antigen (PSA). As another example, troponin is a complex of three proteins that is integral to muscle contraction in skeletal and cardiac muscle, but not smooth muscle. Those three proteins, also called subunits, are known as troponin C, T, and I. The troponin of skeletal and cardiac muscle can also be differentiated from each other. One difference is that the troponin C subunit of troponin in skeletal muscle has four calcium ion binding sites, whereas in cardiac muscle there are only three.

Cardiac troponin I and T are very sensitive and specific indicators of damage to the heart muscle (myocardium). They are measured in the blood to differentiate between unstable angina and myocardial infarction (heart attack) in patients with chest pain. In particular, elevated levels of troponin in the blood is an indicator of damaged heart muscle.

Heart disease is a leading cause of death in the United States. The American Heart Association has estimated that 1.2 million people suffer a heart attack every year and that 40% of them die as a result.

Immediate treatment of a heart attack is important to preserve heart muscle and minimize damage and other long-term consequences to the patient. For example, some treatment therapies can only be administered within certain time windows from onset of symptoms. In addition, some treatments which are given for a heart attack are inappropriate and possibly adverse if the patient turns out to be suffering from something else. It would be desirable to have an assay that can detect the presence of troponin and/or other cardiac markers quickly to confirm the diagnosis of a heart attack.

In another aspect, hepatitis C virus (HCV) is a blood-borne virus. Once a person is chronically infected, the virus is almost never cleared without treatment and HCV is a major cause of chronic hepatitis. Some go on to develop cirrhosis and end-stage liver disease. It would be desirable to be able to test for viruses such as HCV.

Accordingly, the need exists for a relatively rapid device for detecting the presence and/or amount of molecules in biological fluids.

BRIEF DESCRIPTION

Disclosed, in various embodiments, are devices and systems for performing assays. Also disclosed are methods for rapidly performing assays using such devices and systems and methods for making and using such devices and systems.

In embodiments, a test device for quantifying the concentration of an analyte in a biological fluid is disclosed which comprises:
 a housing defining a sample port in a surface of the housing;
 a test strip disposed within the housing; and
 a test well disposed within the housing between the sample port and the test strip;
 wherein the test well defines a flow path to the test strip and includes a mixer and a conjugate, the conjugate comprising a first antibody specific for a first epitope on the analyte and a signal entity; and
 wherein the test strip comprises a first end zone, a second end zone, and a trapping zone between the end zones, the trapping zone having irreversibly bound thereon a second antibody specific for a second epitope on the analyte.

The test device may further comprise a window located in the surface of the housing over the trapping zone of the test strip.

The conjugate may be present in the test well as a lyophilized pellet or a dried film. The conjugate may also be water-soluble.

The mixer may be a magnetic stirrer.

The signal entity may be selected from the group consisting of an enzyme, colored solid particles, fluorescent beads, and fluorescent water-soluble proteins. In particular embodiments, the signal entity may be a fluorescent signal entity or a fluorescent water-soluble protein.

The test strip may further comprise a control zone between the first end zone and the second end zone, the control zone having irreversibly bound thereon the first epitope. In embodiments, the control zone is between the test well and the trapping zone.

The test strip may be made from an absorbent material. The absorbent material may be nitrocellulose. The test strip may further comprise a pad of absorbent material in each end zone.

The test well may further comprise a plastic insert, the plastic insert having a hole which defines the flow path to the test strip.

The test device may further comprise a source for activating the mixer.

In some embodiments, the housing further comprises a window located in the surface of the housing and associated with the trapping zone; the mixer is a magnetic stirrer; the conjugate is present in the test well as a lyophilized pellet or a dried film; and the signal entity is a fluorescent water-soluble protein.

In other embodiments, a test device for detecting the presence or quantifying the concentration of an analyte in a biological fluid is disclosed which comprises:
 a housing defining a sample port and a detection window in a surface of the housing;
 a test strip disposed within the housing, at least a portion of the test strip being associated with the detection window; and
 a test well disposed within the housing between the sample port and the test strip;

wherein the test well defines a flow path to the test strip and includes a magnetic stirrer and a conjugate, the conjugate comprising a first antibody specific for a first epitope on the analyte and a signal entity; and wherein the test strip comprises a first end zone, a second end zone, and a trapping zone between the end zones, the trapping zone having irreversibly bound thereon a second antibody specific for a second epitope on the analyte.

In other embodiments, a system for detecting the presence or quantifying the concentration of an analyte in a biological fluid is disclosed which comprises:

a test device, the device comprising:

a housing defining a sample port and a detection window in a surface of the housing;

a test strip disposed within the housing, at least a portion of the test strip being associated with the detection window; and a test well disposed within the housing between the sample port and the test strip;

wherein the test well defines a flow path to the test strip and includes a mixer and a conjugate, the conjugate comprising a first antibody specific for a first epitope on the analyte and a signal entity; and wherein the test strip comprises two end zones and a trapping zone between the two end zones, the trapping zone having irreversibly bound thereon a second antibody specific for a second epitope on the analyte; and a signal sensing device.

In other embodiments, a signal sensing device is provided. The signal sensing device may comprise:

a processor;

a detection head;

a movable tray capable of holding the test device and moving the detection window under the detection head; and means for detecting a signal generated by the signal entity.

The signal sensing device may further comprise a source for activating the mixer.

The signal entity may be selected from the group consisting of an enzyme, fluorescent beads, fluorescent dots, and fluorescent water-soluble proteins.

The means for detecting a signal may be visual or by a detection device such as a voltage adjustable photomultiplier tube or a charge coupled device. The signal sensing device may further comprise a light source and a light filter. The mixer may be a magnetic stirrer.

In particular embodiments, the signal entity is a fluorescent signal entity; and the signal sensing device further comprises a light source and a light filter.

The signal entity may be an enzyme capable of causing chemiluminescence or bioluminescence.

In other embodiments, a process for detecting the presence or quantifying the concentration of an analyte in a biological fluid is disclosed which comprises:

providing a test device, the device comprising:

a housing defining a sample port and a detection window in a surface of the housing;

a test strip disposed within the housing, at least a portion of the test strip being associated with the detection window; and a test well disposed within the housing between the sample port and the test strip;

wherein the test well defines a flow path to the test strip and includes a mixer and a conjugate, the conjugate comprising a first antibody specific for a first epitope on the analyte and a signal entity; and the test strip comprises two end zones and a trapping zone between the two end zones, the trapping zone having irreversibly bound thereon a second antibody specific for a second epitope on the analyte;

adding the biological fluid through the sample port into the test well;

mixing the conjugate and biological fluid within the test well to form a mixture;

allowing the mixture to flow onto the test strip so that the mixture is transported to the trapping zone; and measuring a signal generated by the signal entity at the trapping zone.

The time between applying the biological fluid and measuring the signal may be from about 15 seconds to about 20 minutes, including about 10 minutes. The stirring step may take place for from about 5 seconds to about 15 minutes, including about 2 minutes. The step of allowing the mixture to flow onto the test strip may take place for from about 5 seconds to about 15 minutes, including about 8 minutes.

The step of allowing the mixture to flow onto the test strip is generally performed by passive means. In some embodiments though, the step is actively performed by regulating the release of the mixture from the test well onto the test strip.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
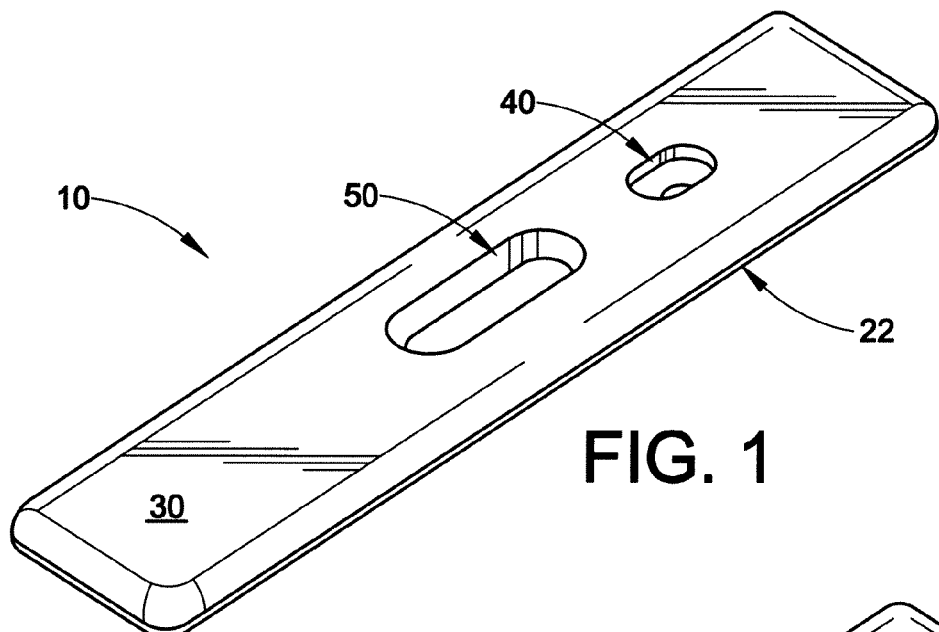
FIG. 1 is one embodiment of a test device of the present disclosure.

A more complete understanding of the devices, processes, and components disclosed herein can be obtained by reference to the accompanying drawings. These drawings are merely schematic representations based on convenience and the ease of demonstrating the present disclosure, and are, therefore, not intended to indicate relative size and dimensions of the devices or components thereof and/or to define or limit the scope of the present disclosure.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The devices, systems, and methods of the present disclosure can be used to detect or quantify the concentration of an analyte in a biological fluid. Such fluids are liquid and include blood, serum, urine, saliva, and/or cellular extracts. The devices can return a result in as little as 10 minutes, which is much faster than current systems for detecting HCV or troponin levels. For example, the IMMULITE 2000 troponin assay, offered by Siemens, requires 30 minutes to provide results. However, a difference of even a couple of minutes would be desirable. The devices can also be used to assay other molecules and proteins as well.

The devices implement what is commonly called a "sandwich assay" for determining the concentration of the analyte. A labeled conjugate comprises a first antibody specific for a first epitope on the analyte and a signal entity. The first antibody binds to the first epitope, thus binding the signal entity to the analyte. A second antibody specific for a second epitope on the analyte is then used to immobilize the analyte (and the signal entity) at a given location. The signal entity can then generate a signal at that location that is proportional to the amount of analyte.

FIG. 1 shows one embodiment of a test device of the present disclosure. The test device 10 comprises a housing 20. The housing 20 has a surface 30 defining a sample port 40. A detection window 50 is also defined by the surface 30. Surface 30 may also be considered an upper surface of the housing 20.

Figure 2:
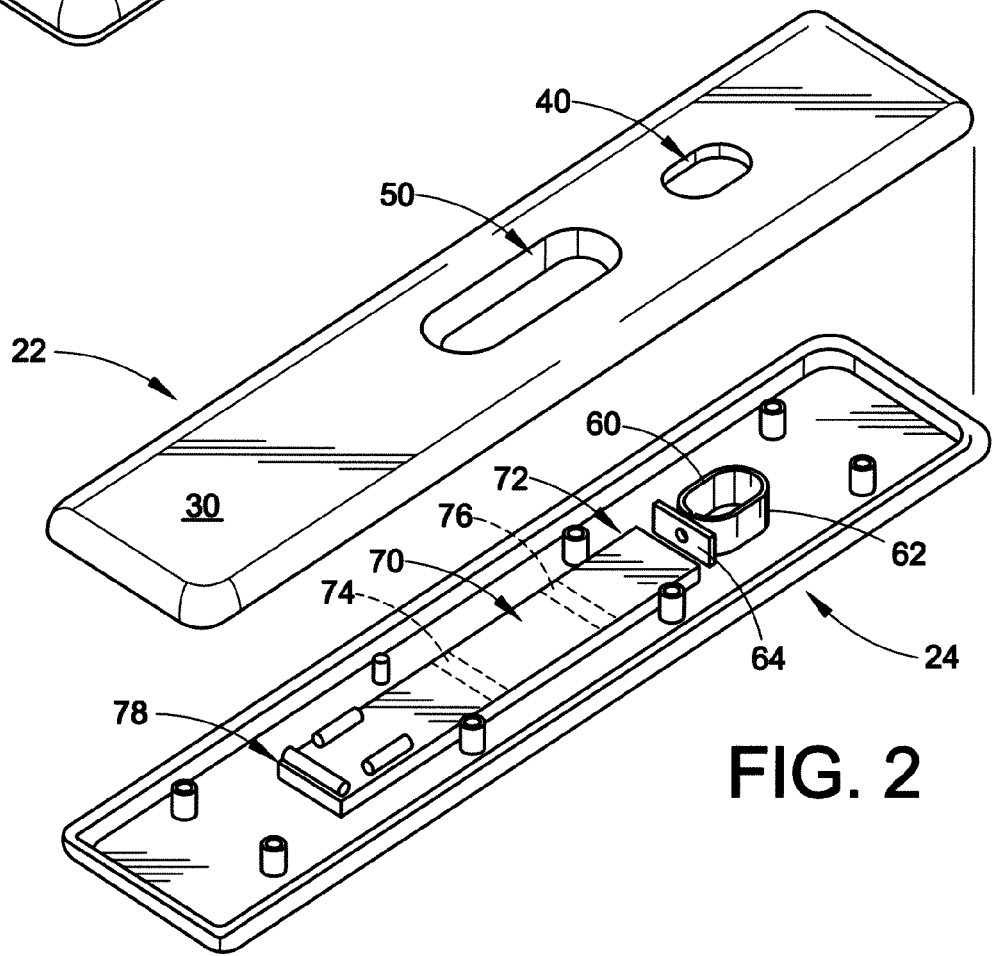
FIG. 2 is shows the interior of a test device of the present disclosure.
Figure 3:
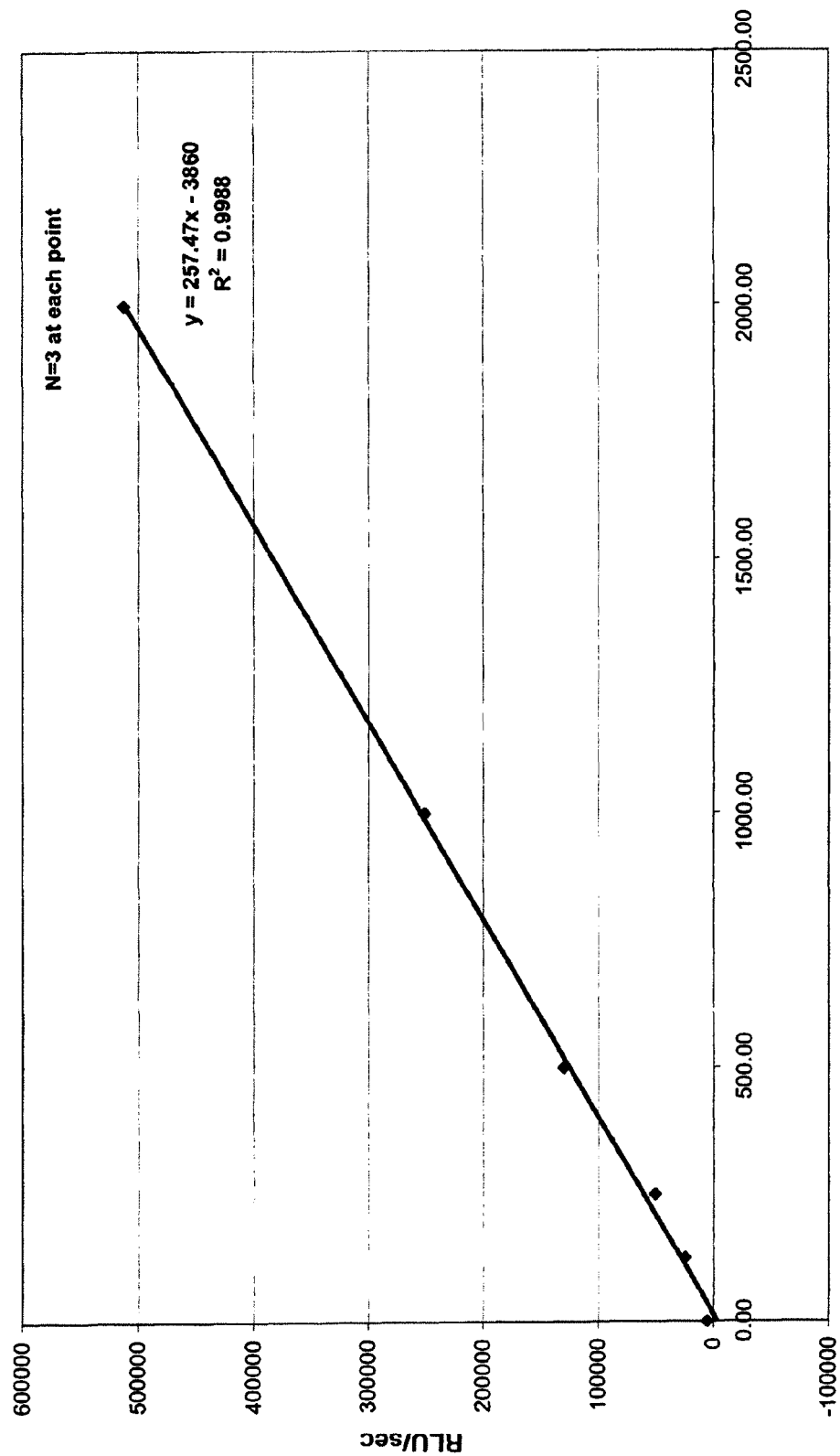
FIG. 3 is a graph showing the correlation between fluorescent output and concentration of analyte.
Figure 4:
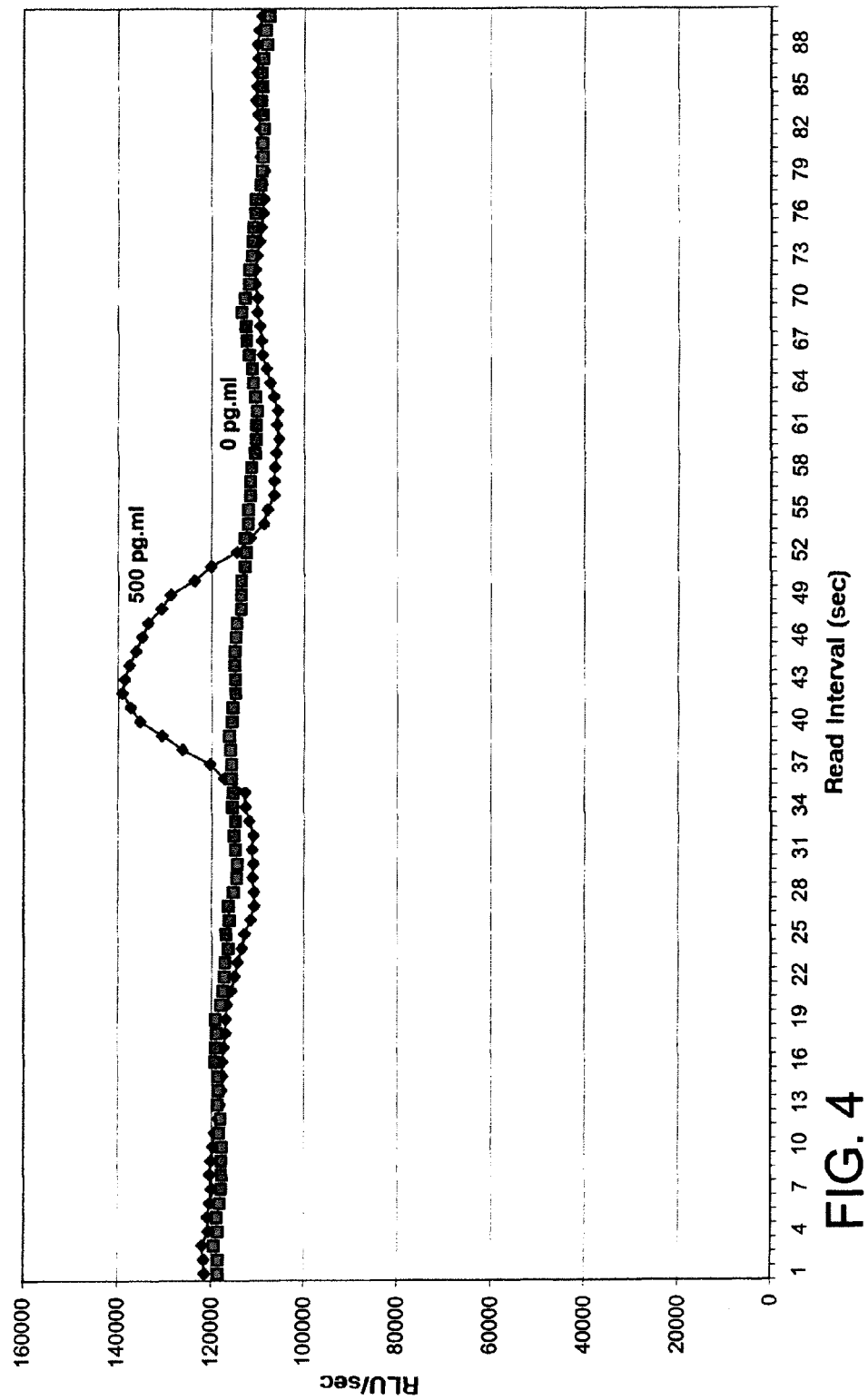
FIG. 4 is a graph showing that analyte can be detected within a minute of completing the assay.

FIG. 2 shows the interior of the housing 20. The housing 20 can be formed from an upper half 22 and a lower half 24, which can be joined together by means known in the art. Disposed within the housing 20 are a test well 60 and a test strip 70. The test well 60 is located between the sample port 40 and the test strip 70. In other words, a fluid sample deposited through the sample port 40 must enter the test well 60 prior to entering the test strip 70. This construction is unlike other systems, where the fluid sample is deposited directly onto the test strip. For example, the sample port may be in the shape of a funnel that directs the fluid sample into the test well.

The test well 60 comprises a sidewall 62, generally arising from the lower half 24 of the housing. The test well 60 also defines a flow path 64 from which fluid exits the test well and contacts the test strip 70. In embodiments, the flow path 64 is a slit in the sidewall 62 that allows fluid to contact the test strip 70. In other embodiments, the flow path 64 is formed by a plastic insert that comprises the test well 60. The plastic insert has a hole defining the flow path 64.

The test well 60 contains a conjugate (not shown). The conjugate may be in the form of a lyophilized pellet or a dried film or some other form which preserves the conjugate in a stable form. The conjugate comprises a first antibody specific for a first epitope on the analyte and a signal entity. The signal entity generates a signal which can be detected. The signal may be, for example, luminescent, chemiluminescent, bioluminescent, fluorescent, or visible. The signal entity can be an enzyme, colored solid particles, fluorescent beads, fluorescent dots, and/or fluorescent water-soluble proteins. For example, the enzymes horseradish peroxidase, alkaline phosphatase, galactosidase, and aequorin, with their appropriate substrates, are commonly employed to produce luminescence. Colored solid particles such as latex or gold may be used to provide a visual signal. Fluorescent beads of different excitation/emission spectra could be employed. Fluorescent water-soluble proteins may also be used. For example, Sensilight™ PBXL dyes, available from Martek, are water-soluble complexes comprising phycobiliproteins such as phycoerythrin and phycocyanin. In embodiments, the entire conjugate is water-soluble.

The test well 60 also contains a mixer or stirrer (not shown). The mixer may be, for example, a magnetic stirrer, such as a piece of magnetized plastic that can be energized by an outside power source to spin. The outside power source can be part of the test device 10 or part of an associated instrument. When a fluid sample is placed into the test well 60 and the mixer is energized, the conjugate will be dissolved and rapidly distributed homogeneously throughout the fluid sample, forming an analyte-conjugate complex in the mixture. This mixing also promotes maximum binding between the analyte and the conjugate, which may increase the reliability of the assay at low concentrations of analyte. In the absence of a mixing mechanism, there is very poor contact between the analyte and the conjugate, resulting in irreproducible movement of complex through the nitrocellulose bed. This can be seen in images as streaking and severe channeling. Streaking and channeling can affect the accuracy of the assay.

The mixture, formed from the fluid sample and conjugate, then flows along the flow path 64 to the test strip 70. The mixture generally flows via passive means to the test strip, but can also be actively controlled, such as by regulating the flow. The test strip 70 is generally made from an absorbent material, such as nitrocellulose. The strip may also have a backing, such as Mylar™, to give support and strength. The test strip 70 comprises a first end zone 72, a second end zone 78, and a trapping zone 74 between the two end zones. Fluid moves through the nitrocellulose matrix as a result of capillary action. The end zone 72 nearest the test well 60 may be considered an upper end and the end zone 78 furthest from the test well 60 may be considered a lower end. Additional pads of absorbent material may be present at either end zone. At the upper end, the pads provide additional capacity for absorbing fluid exiting the test well 60. At the lower end, they absorb excess fluid which has already run through the trapping zone 74.

A second antibody specific for a second epitope on the analyte is irreversibly bound to the test strip in the trapping zone 74. As the mixture passes through the trapping zone 74, analyte (and the conjugate bound to it at the first epitope) is bound to the test strip. The second antibody can be considered a trapping entity which recognizes its binding partner, the analyte, and restricts it to the trapping zone. The presence of the binding partner (analyte) is then detected by the signal entity.

In some embodiments, the test strip 70 further comprises a control zone 76 which has irreversibly bound thereon the first epitope. The control zone 76 between the first end zone 72 and the second end zone 78. The control zone is spaced apart from the trapping zone. In some embodiments, the control zone 76 is located between the test well 60 and the trapping zone 74. The use of the first epitope in the control zone differs from that of other assays which usually use an antibody reactive to the first antibody of the conjugate as a control site. For example, if the first antibody of the conjugate is a mouse antibody, the control site usually uses a goat (or other species) anti-mouse antibody. However, the anti-mouse antibody reacts to the mouse antibody of the conjugate. This type of control does not show that the mouse antibody has retained its ability to recognize the first epitope of the analyte. It also does not give any indication of conjugate integrity (i.e. the first antibody is still bound to the signal entity).

The result of the assay can be read through the detection window 50. The detection window 50 is generally associated with at least a portion of the test strip 70, but can expose the entire test strip as well. In particular, the detection window 50 may associated with the trapping zone 74 as well as the control zone 76 in embodiments having a control zone. More than one detection window may be used, for example one window exposing the trapping zone and a second window exposing the control zone. Depending on the type of signal entity, the test device can be read visually or with use of a related system, such as a fluorimeter or a luminometer.

In other embodiments, the test device comprises part of a system for detecting the presence or quantifying the concentration of an analyte in a biological fluid. The system further comprises a signal sensing device. The signal sensing device comprises a processor; a detection head; a movable tray capable of holding the test device and moving the detection window under the detection head; and means for detecting a signal generated by the signal entity. A source for activating the mixer can also be provided. The processor controls the operation of the signal sensing device, e.g. timing, data collection, etc. The source activates the mixer in the test device. In some embodiments, the source is an electromagnetic device capable of inducing a magnetic stirrer to spin. The signal sensing device may also include a timer for regulating the stir time and the incubation time. The movable tray holds the test device and moves it under the detection head. In particular, the test device is scanned beginning at the end of the detection window nearest the sample port and then down, such that the portion of the test strip associated with the detection window is scanned. This is generally done at a constant, predetermined speed. In this configuration, without filters or light sources, the means for detecting a signal can be a voltage-adjustable photomultiplier tube, a charge coupled device (CCD) system, a Complementary Metal Oxide Semiconductor (CMOS) system, or similar photodetector, and the signal sensing device can be used as a luminometer for luminescence detection.

Alternatively, the test device can simply be read visually.

In other embodiments, the signal sensing device further comprises a light source and a light filter. In these embodiments, the signal sensing device can additionally be used as a fluorimeter for measuring fluorescence. The light source may be a light emitting diode (LED) and in embodiments, two LEDs are used in the signal sensing device. The light source should emit the appropriate excitation wavelengths and their illumination may be adjusted as required. The light filters are those necessary for detection of the fluorescent signal. Light from the light source can be transported to the detection head via optical fibers and the emission illumination from the signal entity can be transported to the means for detecting a signal (such as a photomultiplier tube or photodetector) by similar means. The signal sensing device may be handheld.

The total assay run time depends on the time needed to stir the analyte and conjugate together and the incubation time needed to allow the mixture to flow through the trapping zone. In embodiments, the total assay run time is from about 15 seconds to about 20 minutes. The stir time may be as low as two minutes and an optimal incubation time is eight minutes, giving a total assay run time of about 10 minutes. Generally, the stir time and incubation time are each from about 5 seconds to about 15 minutes. Usually, the incubation time is longer than the stir time. The test device can then be read in the signal sensing device. It should be noted that following the stir cycle, the test strip can be scanned and indicate the binary presence (yes or no) of analyte present in the trapping zone anytime during the incubation time as well. This might be of importance if presence of the analyte alone provides information and time is critical, such as for emergency chest pain patients wherein the analyte is troponin. In particular, there is no time-consuming wash step in the assay.

In other embodiments, a process for detecting the presence or quantifying the concentration of an analyte in a biological fluid comprises providing a test device as disclosed herein. A biological fluid is added through the sample port into the test well. The conjugate and biological fluid are mixed within the test well to form a mixture. The mixture is allowed to flow onto the test strip so that the mixture is transported to the trapping zone. The signal generated by the signal entity at the trapping zone is then measured. The time between adding the biological fluid and measuring the signal is about 10 minutes. The stirring step can take place for about 2 minutes. The step of allowing the mixture to flow onto the test strip can take place for about 8 minutes. The step of allowing the mixture to flow onto the test strip can be actively performed by regulating the release of the mixture from the test well onto the test strip.

The assay can detect (reveal) the presence of analyte based on the location on the test strip in which the signal is located. For example, detection of a signal from the trapping zone or control zone will generally indicate that analyte is present. The assay can also quantify the concentration of the analyte based on the strength of the signal. Methods for creating a reference table that correlates signal strength to concentration are well-known in the art. Further embodiments of the process include comparing the strength of the signal to a reference to determine the concentration of the analyte.

The test devices, methods, and assays of the present disclosure can also be set up for multiplexing. In other words, rather than detecting only one analyte with one test device, the test device can be set up to detect multiple analytes in a single assay. This can be done by including additional conjugates in the test well, where each conjugate is specific for a given analyte, and binding additional antibodies in the trapping zone, where each antibody is specific for a given analyte. To differentiate between analytes, the signal produced by the signal entity on each conjugate should be uniquely distinguishable. For example, in a system that detects two analytes, the signals could be fluorescence at different wavelengths. Put another way, each analyte should have a specific signal that distinguishes it from every other analyte.

The devices and methods of the present disclosure are further illustrated in the following non-limiting examples.

EXAMPLES

In Examples 1 and 2, the presence of troponin I (cTNI) was examined in a serum sample. cTNI served as the analyte.

Test Device

The test device was a black plastic cassette designed with a detection window and sample port on its upper surface.

Test Strip

The test strip was comprised of mylar backed nitrocellulose. At either end of the strip were individual pieces of absorbent material. The strip was placed into the cassette such that the face of the nitrocellulose test strip was open to the detection window in the upper part of the housing.

Antibodies

One mouse monoclonal antibody (TPC110) and one goat antibody (P4), directed at two different epitopes of cTNI, were used for the detection of cTNI. One antibody (P4) was cleaved by pepsin to create an $Fab'_2$ fragment. The $Fab'_2$ fragment was further treated with a thiol reagent to yield an Fab' fragment. The Fab' fragment was biotinylated and then overlaid on a neutravidin zone, which was pre-deposited in the nitrocellulose matrix. The zone formed a line across the test strip. The neutravidin zone served as the trapping zone of the nitrocellulose test strip and the P4 antibody served as the second antibody.

The other antibody (TPC110) was treated similarly, with the exception that at the Fab' stage, the Fab' fragment was coupled to a highly fluorescent phycoerythrin derivative (Sensilight™ PBXL-3, available from Martek Biosciences Corp.) to form a conjugate. The TPC110 antibody served as the first antibody and the phycoerythrin derivative served as the signal entity. The phycoerythrin derivative is excited by 610 nm radiation and emits light at 670 nm.

Meter

The radiation emitted by the phycoerythrin derivative was quantified through either a cooled charge coupled diode (CCD) (Night Owl, Berthold Industries) or with custom designed scanning fluorimeter.

The scanning fluorimeter was a small, relatively inexpensive and portable device that can be powered conventionally or through rechargeable batteries. It can be allied to a PC (via an RS2 port) for data analysis. The light sources were two light emitting diodes (LED) of the appropriate excitation wavelengths. The housing of the fluorimeter was equipped with the necessary excitation/emission filters for phycoerythrin detection. Light detection was achieved through the use of a voltage adjustable photomultiplier tube (PMT). The cassette holder was a movable tray, which passes underneath a reading head at a predetermined rate of movement. Light from the LEDS was transported to the read head via optical fibres. The emission illumination from the excited phycoerythrin was channelled to the PMT in a similar fashion. Below the scanning bed was a small, single speed magnetic stirrer. The stir time was nominally set to two minutes following addition of the fluid sample to the lyophilized conjugate within the sample port. An adjustable incubation period can also be programmed into the reader and was set to thirteen minutes (total assay run time of 15 minutes). At thirteen minutes, the device automatically scanned the surface of the nitrocellulose test strip for signal detection and PMT voltage adjustment.

Assay Characteristics

The sample port of the cassette opened into a test well separated from the test strip by a thin plastic insert having a small hole in its center. The TPC110 conjugate was lyophilized in the test well, along with a small square of magnetized plastic.

The fully assembled device was placed onto the receiving tray within the fluorimeter. The stir cycle was set to two minutes and the incubation period to 13 minutes, giving a total run time of 15 minutes. At the completion of 15 minutes, the tray retracted, positioning the upper rim of the detection window (adjacent to the sample port) directly below the read head. The tray retraced its steps, at a constant predetermined speed, such that the length of nitrocellulose, exposed to the detection window was scanned.

The detection of signal within the trap zone against a constant fluorescent background relied on rapid and irreversible capture of the cTNUTPC110-phycoerythrin complex and on the highly fluorescent output of the trapped phycoerythrin derivative.

It should be noted that there was no wash step in this procedure. The elimination of a washing step allowed for a rapid turn around time for assay results (15 min.).

Samples of cTNI, in cTNI free serum, were prepared using NIST Standard Reference Material 2921. SRM 2921 is a complex of cTNI, containing troponins I, C and T. SRM 2921 is the standard recommended for use in cTNI assays by the American Association of Clinical Chemists and the American College of Cardiologists.

A level of cTNI (100 ng/ml) was prepared and used as the starting concentration for dilution in the preparation of calibrators of lower value. The starting concentration (100 ng/ml) was diluted with cTNI free serum in all cases. The volume of serum added to the sample port was 150 μl.

To initiate the assay, the cassette was placed in its receiving tray within the scanning fluorimeter. Sample (150 μl) was added to the lyophilized pellet within the sample cup. The stir cycle was initiated, stimulating dissolution of the conjugate and rapid, homogeneous distribution of the conjugate within the sample.

The small hole in the plastic insert effectively metered the flow of fluid into the nitrocellulose test strip, thereby increasing the contact time between the analyte and conjugate in the test well and allowing more efficient solution binding kinetics to occur.

In the presence of cTNI, the antibody component of the conjugate bound to a specific epitope on the cTNI protein to form cTNI-TPC110-phycoerythrin complexes. These complexes migrated through the nitrocellulose test strip by means of capillary action. As the complexes passed through the trapping zone (containing P4 Fab'), the P4 antibody fragment bound to a different epitope on cTNI. Since the P4 Fab' was irreversibly bound to the nitrocellulose, any P4-cTNI-TPC110-phycoerythrin complex was similarly bound.

Over the time period of 15 minutes, increasing amounts of complex were trapped, resulting in a fluorescent signal whose intensity was proportional to the concentration of cTNI in the sample. In the absence of cTNI in the sample, none of the binding events would occur, which limits the signal to that of the inherent background fluorescence of the diluted conjugate.

After completion of the 15 minute cycle, the strip was scanned along its length.

Example 1

Calibration levels of 0, 125, 250, 500, 1000, and 2000 pg/ml cTNI in serum were run through the device using the procedures described above. The results were graphed and are seen in FIG. 3. A straight-line correlation ($r^2$=0.9988) between the concentration and the fluorescent output is indicated.

Example 2

A serum sample containing 500 pg/ml cTNI was placed in the device and the stir cycle run for two minutes. Three minutes after the cycle ended (i.e. 5 minutes total assay run time), the trapping zone was continuously scanned. Data was recorded every second. A sample containing no cTNI (i.e. a negative sample) was similarly processed. FIG. 4 is a graph of the results. The graph shows the fluorescent output (RLU/sec) versus the read interval (sec), where 0 corresponds to 5 minutes total assay run time. The 500 pg/ml sample began rising above the negative sample at a read interval of about 35 sec and peaked at about 41 sec, or about 5 minutes 41 seconds total assay run time. The graph showed that cTNI can be detected at a relatively low abundance within a minute of completing the stir and incubation cycles. A baseline was visible at both concentrations (0 and 500 pg/ml). Thus, cTNI was detectable at low levels and within an early time frame.

Example 3

A series of serum samples were obtained from infected and non-infected individuals. The assay was used to determine the level of anti-HCV antibodies in each sample. The measurements were performed using a Night Owl instrument. The configuration of the strip and cassette remained the same, with the exception that a cocktail of peptides, from known epitopes of the HCV genome, were utilized as the trapping entities (i.e. second antibody). The trapping entities were biotinylated at the N-terminal residue and then overlaid on a neutravidin zone. The fluorescent signal entity used in the conjugate was goat anti-human phycoerythrin.

The procedure used was identical to that described above, with the exception that the sample was stirred using a standard magnetic stir plate. The images were captured on the Night Owl using a 20 msec exposure at 5 or 10 minute total assay run times. The number of DNA copies for each sample was provided by the sample supplier (Promeddx Inc.); a level of less than 200,000 was considered negative.

The data from this experiment is shown in Table 1 below. As can be seen, negative sera gave a light output of 440,000 RLU/SEC or less at 5 minutes. Positive sera emitted light at >640,000 RLU/SEC at 5 minutes.

TABLE 1

| Sample ID | # DNA copies | Total Assay Run Time (min) | Light Output (RLU/sec) |
|---|---|---|---|
| 9991145 | 3,300,000 | 5 | 2,675,594 |
|  |  | 10 | 4,603,162 |
| 9991149 | 1,000,000 | 5 | 2,102,772 |
|  |  | 10 | 3,559,970 |
| 9990993 | <200,000 | 5 | 318,991 |
|  |  | 10 | 367,046 |
| 9990974 | <200,000 | 5 | 437,098 |
|  |  | 10 | 485,174 |
| 9990966 | 210,000 | 5 | 639,367 |
|  |  | 10 | 758,388 |
| 9810020 | 7,900,000 | 5 | 792,129 |
|  |  | 10 | 1,100,581 |

Example 4

The assay was modified to demonstrate its application to the detection of small molecules (<2,000 Daltons). A peptide trap line was made by attaching a peptide epitope (recognized by the M155-phycoerythrin conjugate) to bovine serum albumin and depositing it on the nitrocellulose test strip. A neutravidin line was then laid down on the lower end of the test strip. In other words, fluid had to flow through the peptide trap line before reaching the neutravidin line. The M155-phycoerythrin conjugate was then modified by reaction with biotin.

The theory behind the design of this assay is that in the absence of peptide, no analyte-conjugate complex is formed. The conjugate can thus still bind to the epitope on the peptide trap line. In the presence of peptide, an analyte-conjugate complex is formed which prevents binding to the peptide trap and allows said complex to continue its movement through the nitrocellulose past the peptide trap line. Upon encountering the neutravidin line, the biotin molecule present in the conjugate binds to neutravidin, thereby holding the conjugate in the neutravidin line. In other words, the peptide trap line served as the trapping zone and the neutravidin line served as the control zone.

Figure 5:
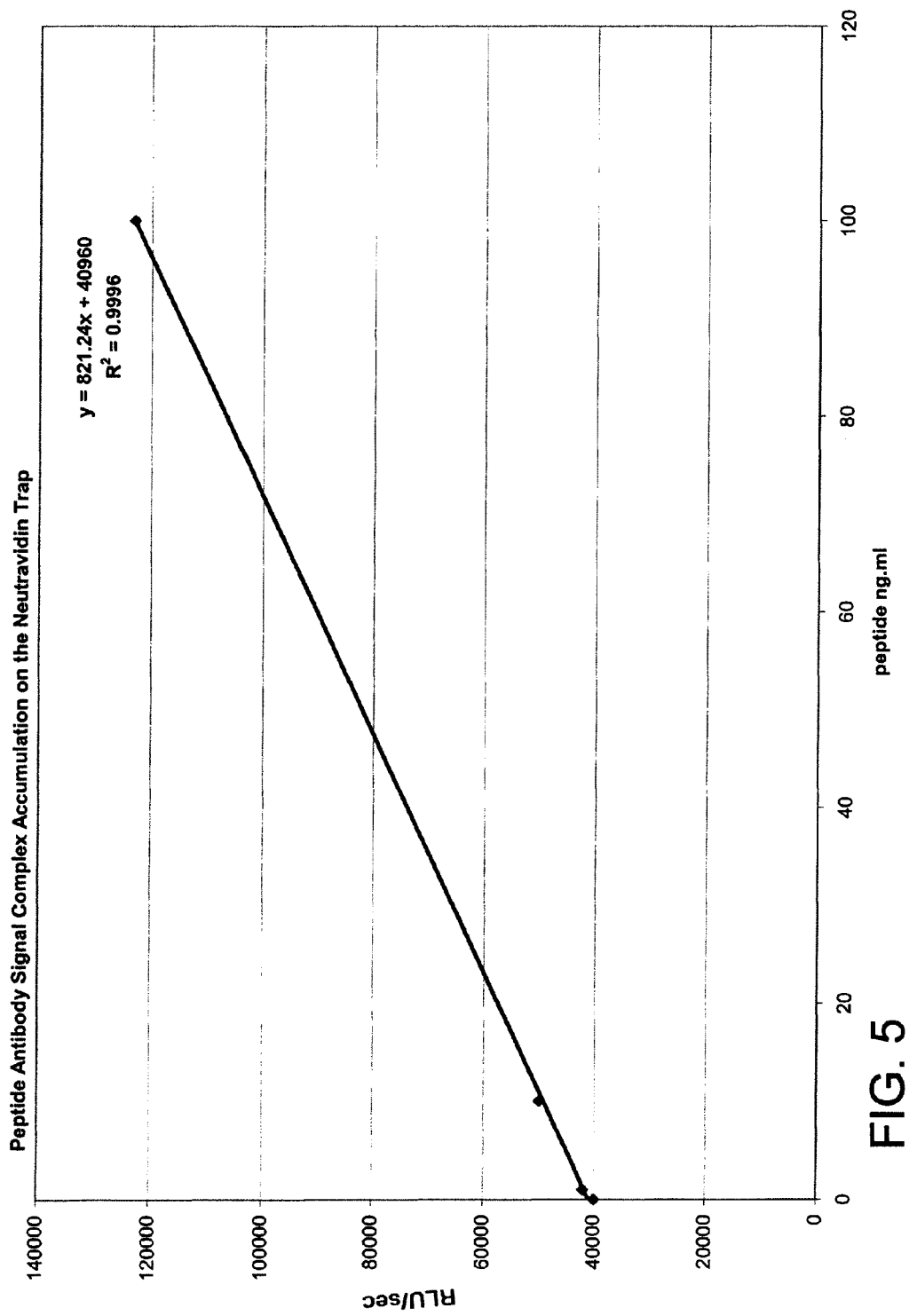
FIG. 5 is a graph illustrating the use of a control line in detecting or quantifying analyte.

A range of peptide concentrations was prepared in serum (0, 1, 10, and 100 ng/ml). The results can be seen in FIG. 5. In the images, the peptide trap line was on the right hand side and the neutravidin line was on the left. At 0 ng/ml, there was strong fluorescence from the peptide trap line and weak fluorescence from the neutravidin line. With increasing concentration of peptide, there was increased trapping on the neutravidin zone and decreased accumulation of conjugate on the peptide line. Over the range of 0 to 100 ng/ml, the relative RLU/sec for the peptide trap line decreased from 190,000 at 0 ng/ml down to 115,000 at 100 ng/ml (a net loss of 75,000). For the neutravidin line, the relative RLU/sec increased from 40,000 at 0 ng/ml to 123,000 at 100 ng/ml (a net gain of 83,000).

This type of assay is readily adapted to the measurement of small drug entities and could also be applied to large molecules themselves.

The devices and methods of the present disclosure have been described with reference to exemplary embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

The invention claimed is:

1. A system for detecting the presence or quantifying the concentration of an analyte in a biological fluid, comprising:
   a test device, the device comprising:
      a housing defining a sample port and a detection window in a surface of the housing;
      a test strip disposed within the housing, at least a portion of the test strip being associated with the detection window; and
      a test well disposed within the housing between the sample port and the test strip;
      wherein the test well defines a flow path from the sample port to the test strip and includes a mixer and a conjugate, the conjugate comprising a first antibody specific for a first epitope on the analyte and a signal entity; and
      wherein the test strip comprises two end zones and a trapping zone between the two end zones, the trapping zone having irreversibly bound thereon a second antibody specific for a second epitope on the analyte; and
   a signal sensing device, the signal sensing device comprising:
      a processor;
      a detection head;
      a movable tray capable of holding the test device and moving the detection window under the detection head; and
      means for detecting a signal generated by the signal entity.

2. The system of claim 1, further comprising a source for activating the mixer.

3. The system of claim 1, wherein the signal entity is selected from the group consisting of an enzyme, fluorescent beads, fluorescent dots, and fluorescent water-soluble proteins.

4. The system of claim 1, wherein the means for detecting a signal is a voltage adjustable photomultiplier tube, a charge coupled device (CCD) system, or a Complementary Metal Oxide Semiconductor (CMOS) system.

5. The system of claim 1, wherein the signal sensing device further comprises a light source and a light filter.

6. The system of claim 1, wherein the signal entity is a fluorescent signal entity; and the signal sensing device further comprises a light source and a light filter.

7. The system of claim 1, wherein the signal entity is an enzyme capable of causing chemiluminescence or bioluminescence.

8. A process for detecting the presence or quantifying the concentration of an analyte in a biological fluid, comprising:
   providing a test device, the device comprising:
      a housing defining a sample port and a detection window in a surface of the housing;
      a test strip disposed within the housing and associated with the detection window; and
      a test well disposed within the housing between the sample port and the test strip;
   wherein the test well defines a flow path from the sample port to the test strip and includes a mixer and a conjugate, the conjugate comprising a first antibody specific for a first epitope on the analyte and a signal entity; and
   wherein the test strip comprises two end zones and a trapping zone between the two end zones, the trapping zone having irreversibly bound thereon a second antibody specific for a second epitope on the analyte;
   adding the biological fluid through the sample port into the test well;
   mixing the conjugate and the biological fluid within the test well to form a mixture;
   allowing the mixture to flow onto the test strip so that the mixture is transported to the trapping zone; and
   measuring a signal generated by the signal entity in the trapping zone using a signal sensing device, the signal sensing device comprising:
      a processor;
      a detection head;
      a movable tray capable of holding the test device and moving the detection window under the detection head; and
      means for detecting a signal generated by the signal entity.

9. The process of claim 8, wherein the time between adding the biological fluid and measuring the signal is from about 15 seconds to about 20 minutes.

10. The process of claim 8, wherein the mixing step takes place for about 2 minutes.

11. The process of claim 8, wherein the step of allowing the mixture to flow onto the test strip takes place for about 8 minutes.

12. The process of claim 8, wherein the step of allowing the mixture to flow onto the test strip is performed by regulating the release of the mixture from the test well onto the test strip.

13. The process of claim 8, further comprising the step of comparing the strength of the signal to a reference to quantify the concentration of the analyte.

* * * * *